United States Patent [19]

Conway et al.

[11] 4,308,264
[45] Dec. 29, 1981

[54] STABILIZED, DILUTE AQUEOUS PREPARATION OF 1α,25-DIHYDROXYCHOLECALCIFEROL FOR NEONATAL ADMINISTRATION

[75] Inventors: Nancy M. Conway, Mundelein; Lewis I. Krimen, Lake Bluff, both of Ill.

[73] Assignee: Abbott Laboratories, North Chicago, Ill.

[21] Appl. No.: 228,870

[22] Filed: Jan. 28, 1981

[51] Int. Cl.$^3$ ............................................. A01N 45/00
[52] U.S. Cl. .................................................... 424/236
[58] Field of Search ...................... 424/236; 260/397.2

[56] References Cited

U.S. PATENT DOCUMENTS 3,149,037 9/1964 Aiello et al. ..................... 424/236
4,248,867 2/1981 Ikushima et al. ................. 424/236

Primary Examiner—Elbert L. Roberts
Attorney, Agent, or Firm—John J. McDonnell

[57] ABSTRACT

1α,25-Dihydroxycholecalciferol, also known as 1α,25-dihydroxyvitamin $D_3$, calcitriol or 1α,25(OH)$_2$D$_3$, occurs naturally in man as the active form of cholecalciferol or vitamin $D_3$. The natural supply of vitamin $D_3$ depends on the conversion of 7-dehydrocholesterol to vitamin $D_3$ in the skin by ultraviolet light. Vitamin $D_3$ is then converted to calcitriol in a two-step process in the liver and kidney before its acts on its target tissue.

20 Claims, No Drawings

STABILIZED, DILUTE AQUEOUS PREPARATION OF 1α,25-DIHYDROXYCHOLECALCIFEROL FOR NEONATAL ADMINISTRATION

BACKGROUND OF THE INVENTION

1α,25- Dihydroxycholecalciferol is represented by the formula:

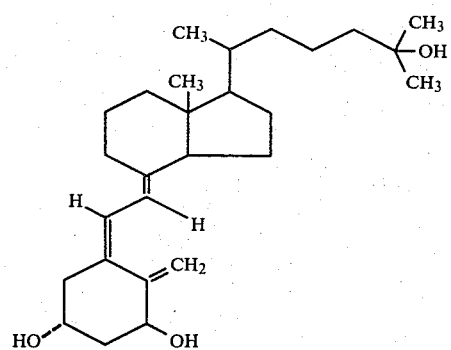

The compound has a molecular weight of 416.647, a molecular formula of $C_{27}H_{44}O_3$, is soluble in organic solvents and practically insoluble in water.

The generic name of 1α,25-dihydroxycholecalciferol is calcitriol.

1α,25-Dihydroxycholecalciferol stimulates intestinal calcium and phosphorus absorption and, with parathyroid hormone, stimulates bone calcium resorption or mobilization. 1α,25-Dihydroxycholecalciferol meets the criteria of a classic steroid hormone in that it is synthesized in one organ under closely regulated conditions, and is then transported by the circulation to another organ where it exerts its biological effects.

The discovery that the kidney is the exclusive site for the production of 1α,25-dihydroxycholecalciferol from 25-hydroxycholecalciferol provided an explanation for the vitamin D-resistant state observed in patients with chronic uremia. Blood levels of 1α,25-dihydroxycholecalciferol in patients with chronic renal failure are low or undetectable. The successful chemical synthesis of 1α,25-dihydroxycholecalciferol made this metabolite available for replacement therapy, and its clinical use for the treatment of hypocalcemia in patients on renal dialysis has recently been approved.

The effectiveness of this drug in several other clinical conditions has been reported in the scientific literature. These investigational uses of 1α,25-dihydroxycholecalciferol include the treatment of renal osteodystrophy, hypoparathyroidism, osteomalacia, osteoporosis, hepatic osteodystrophy, vitamin D-resistant rickets, vitamin D-dependent rickets, childhood renal failure and neonatal hypocalcemia.

Neonatal hypocalcemia is the most prevalent hypocalcemic state encountered in pediatrics and can be divided into two main groups: (1) "early" neonatal hypocalcemia beginning in the first 48 hours of life and (2) "late" neonatal hypocalcemia beginning at the end of the first week of life.

Nearly all infants experience a normal fall in serum calcium during the first few days of life. Early neonatal hypocalcemia appears to be an accentuation of this normal fall in serum calcium, and is often defined as a serum calcium $\leq 7$ mg/dl or $\leq 8$ mg/dl for full term infant or a serum ionized calcium level of from about 3 to 3.5 mg/dl. Minimal serum calcium values are reached at 24-48 hours of age with a gradual return to normal in the next few days. Early neonatal hypocalcemia is frequently accompanied by hyperphosphatemia. In unusual circumstances, early neonatal hypocalcemia may persist for a week or more, and this condition has been called transient congenital idiopathic hypoparathyroidism. Approximately one-third of premature infants ($\leq 7$ weeks gestation), one-third of infants with birth asphyxia (1 minute apgar score of $\leq 6$) and one-half of infants of insulin-dependent diabetic mothers have nearly neonatal hypocalcemia.

Low serum ionized calcium level is associated with serious signs including seizures, apnea, vomiting, neuromuscular irritability, gastric atony, cyanosis and lethargy. Hypocalcemia can also occur without signs of neuromuscular hyperirritability. Correlation of clinical signs with serum calcium levels has been difficult because of the many clinical variables coexistant with hypocalcemia in these high risk infants.

Late neonatal hypocalcemia usually occurs in full term or premature infants who have been started on feedings and who show signs or symptoms of hypocalcemia only after several days or weeks of feedings. The hypocalcemia appears to be precipitated by the high phosphate load of most feedings other than human milk. The high phosphate serum concentration in serum of infants in the first few weeks is associated with low parathyroid hormone levels and with a low glomerular filtration rate.

Clinical manifestations of late neonatal hypocalcemia are similar to those described above in connection with early neonatal hypocalcemia. An electrocardiographic sign, prolonged QT interval, can also be present.

1α,25-Dihydroxycholecalciferol has been shown to be effective in the prophylaxis of neonatal hypocalcemia, however, the preparation of formulations suitable for parenteral administration to neonates has posed a problem due to the irritating nature of the oil-based vehicles used to date for such preparations. In the case of formulations suitable for neonatal administration, it is highly desirable to provide an aqueous parenteral formulation. Prior to the present invention, attempts to provide dilute, aqueous, oil-free solutions of 1α,25-dihydroxycholecalciferol suitable for administration to infants have failed because of the extreme sensitivity of the material to oxidation, and hence its instability in aqueous solutions. In the case of dilute solutions, if even a small percentage of drug oxidizes, it is impossible to obtain a stable solution.

Thus, there has been a long-standing need to provide an oil-free, stable, dilute aqueous solution of 1α,25-dihydroxycholecalciferol suitable for oral or parenteral administration to neonates. The present invention fulfills that need and eliminates the need of employing oil base formulations. U.S. Pat. Nos. 3,384,545; 3,070,499; 3,089,922 and British Pat. No. 905,016 describe vitamin D formulations but those formulations are not suitable for 1α,25-dihydroxycholecalciferol because of this compound's extreme lability to oxygen in dilute aqueous solution.

SUMMARY OF THE INVENTION

The present invention provides a stable, dilute aqueous solution of 1α,25-dihydroxycholecalciferol suitable for oral or parenteral administration to neonates for the treatment of neonatal hypocalcemia. According to the present invention, 1α,25-dihydroxycholecalciferol is solubilized in a nonionic surfactant and stabilized with a combination of an ascorbate and a chelating agent in the presence of an inert atmosphere under carefully controlled pH. The present invention also provides a method for solubilizing 1α-dihydroxycholeciferol in water without employing an oil-solubilizing agent and subsequently stabilizing the aqueous solution.

DETAILED DESCRIPTION OF PREFERRED EMBODIMENTS

The present invention provides a dilute, stable, sterile, nonpyrogenic, aqueous formulation of 1α,25-dihydroxycholecalciferol suitable for oral or parenteral administration to neonates. In the case of parenteral administration, the intramuscular route is preferred.

Generally speaking, the dilute, stable, sterile, nonpyrogenic, aqueous solution comprises one part by weight of 1α,25-dihydroxycholecalciferol; from 1,000 to 15,000 parts by weight of ascorbic acid or a metal ascorbate, preferably from 8,000 to 12,00 parts by weight, and most preferably 10,000 parts by weight; from 100 to 10,000 parts by weight of a chelating agent, preferably from 500 to 2,000 parts by weight and most preferably 1,000 parts by weight; from about 400 to 80,000 parts by weight of a nonionic surfactant, preferably from about 1,000 to 5,000 parts by weight and most preferably 4,000 parts by weight; water q.s. and nitrogen gas q.s., and has a pH of from about 6.5 to 7.8, preferably from 7.0 to 7.5 and most preferably from 7.0 to 7.2 by use of a biologically compatible buffering agent. It is preferable for the solution to be isotonic.

The nonionic surfactant solubilizing agents which may be used in accordance with the invention comprise generally the polyoxyalkylene compounds, e.g., the mono-fatty acid esters of polyethylene glycol, the partial esters of fatty acids and polyhydric alcohols, or the anhydrides of such alcohols, etherified with polyalkylene oxides. In particular may be mentioned such compounds as sorbitan monolaurate-(ethylene oxide)$_{20}$, the analogous compounds containing palmitic or oleic acid and propylene glycol monostearate-(ethylene oxide)$_{25}$. Because of its outstanding solubilizing effectiveness and low toxicity, the preferred solubilizing agent is polyethylene glycol monoricinoleate having from about 30 to about 50 oxyethylene groups per molecule. Those surfactants described in Merck Index, 9th Edition, pp 985, 7360. Those skilled in the chemical art will recognize a variety of pharmaceutically acceptable nonionic surfactants.

The preferred buffering agents are a combination of monobasic and dibasic sodium phosphate, employed in a ratio of approximately 1.84 to 7.6 or 1,844 and 7,600 parts by weight, respectively.

The use of a proper buffering system to carefully control the pH of the solution and employing a combination of effective antioxidant amounts of a metal ascorbate, a chelating agent and an inert atmosphere to combat oxidation is critical to the practice of this invention.

It is wholly surprising that so many parameters are critical to the solution of the problem of providing a stable, dilute aqueous solution of 1α,25-dihydroxycholecalciferol free from the irritating, nonaqueous vehicles employed in conventional preparations. However, the difficulty encountered by those skilled in the art of providing a solution to a long-standing problem is understood when the number of critical parameters required in the practice of this invention are appreciated.

In the preferred embodiments of this invention, the stable, aqueous, dilute sterile 1α,25-dihydroxycholecalciferol solution for parenteral or oral administration is supplied in unit dose 1 ml amber glass ampuls, having the headspace filled by an inert atmosphere such as nitrogen, and which are stored at temperatures of from about 2° to 8° C. in a darkened area.

Each 1 ml of solution preferably contains 1.0 mcg of 1α,25-dihydroxycholecalciferol, 4.0 mg of TWEEN ® polysorbate 20 nonionic surfactant, 1.50 mg of sodium chloride, 10.00 mg of sodium ascorbate, 7.6 mg of dibasic sodium phosphate, 1.84 mg of monobasic sodium phosphate, 1.00 mg of disodium edetate, water, q.s. and nitrogen q.s..

Generally speaking, oral dosages of 1 mcg daily and parenteral dosages of from about 0.02–0.05 mcg/kg daily are effective in the treatment of neonatal hypocalcemia. It is understood that all ingredients will be of a pharmaceutically acceptable grade and quality to make a pharmaceutical dosage form.

The stabilized, aqueous solution of the present invention must be prepared under an inert atmosphere, such as nitrogen or argon, in order to insure that no oxidation takes place. As stated earlier, an inert atmosphere alone, however, is not sufficient to prevent oxidation of the vitamin D metabolite, but must be employed in combination with a metal ascorbate antioxidant and a chelating agent at the proper pH.

In order to prepare the solution of this invention, the nonionic surfactant is heated in a glass-lined or 316 or higher temper grade stainless steel vessel to a temperature of between 50° to 75° C. Nitrogen gas protection is maintained in the vessel headspace throughout the preparation. After the surfactant has been heated to the desired temperature, the 1α,25-dihydroxycholecalciferol is added to the heated surfactant with mixing. Mixing is continued until the 1α,25-dihydroxycholecalciferol has dissolved and the mixture is uniform, providing a concentrate which is then allowed to cool.

Thereafter, an aqueous solution is prepared by heating approximately 110% of the total volume of water for injection to a temperature of between 85° to 100° C. and cooling under a nitrogen atmosphere to a temperature of between 20° to 50° C. in a glass lined or 316 or higher temper grade stainless steel mixing tank. The previously boiled and cooled water for injection is added to approximately 90% of the final volume in a glass-lined or 316 or higher temper grade stainless steel vessel. The buffering agents, sodium chloride, metal ascorbate and chelating agents are then dissolved in the water with mixing under a nitrogen atmosphere and the pH range is checked to insure it is in the desired range. The 1α,25-dihydroxycholecalciferol/nonionic surfactant concentrate is added to the aqueous solution with gentle stirring under a nitrogen atmosphere and water for injection from the above step is added q.s. to final volume. The solution is then aseptically filtered under an inert atmosphere and filled in the desired volume into sterile, dry one ml ampuls. The product is protected with filtered nitrogen gas in the ampul headspace prior to sealing.

The following example further illustrates the present invention.

EXAMPLE 1

Eight thousand sterile ampuls with a nominal fill of 1.25 ml per unit were filled with a sterile, stable, aqueous solution of 1α,25-dihydroxycholecalciferol and having the following composition:

| Ingredient | Amount per ml |
| --- | --- |
| 1α,25-Dihydroxycholecalciferol | 1.0 mcg |
| TWEEN ® polysorbate 20 surfactant | 4.0 mg |
| Sodium chloride | 1.5 mg |
| Sodium ascorbate | 10.0 mg |
| Sodium phosphate, dibasic | 7.6 mg |
| Sodium phosphate, monobasic | 1.84 mg |
| Disodium edetate | 1.0 mg |
| Nitrogen | q.s. |
| Water | q.s. | and prepared as follows:

Forty grams of TWEEN ® polysorbate 20 nonionic surfactant is heated in a 316 temper grand stainless steel vessel to 60° C. under a nitrogen atmosphere. To the heated surfactant are added 11.5 g of 1α,25-dihydroxycholecalciferol with mixing under a nitrogen atmosphere. Maintaining nitrogen protection, the two ingredients are mixed until the 1α,25-dihydroxycholecalciferol is dissolved and the mixture is uniform. The concentrate is then cooled to room temperature.

While the concentrate is cooling, approximately 11 liters of water for injection are heated to 100° C. and cooled under nitrogen gas protection in a glass-lined mixing tank. Approximately 90% of the final volume of the water for injection is added to a glass-lined vessel under a nitrogen atmosphere. To the cooled water are added 15.0 g of sodium chloride, purified crystals, 100.0 g of microcrystalline sodium ascorbate, USP grade, 76.0 g of reagent grade dibasic sodium phosphate, 18.4 g of monobasic sodium phosphate USP granules (monohydrate) and 10.0 g of USP grade disodium edetate, and the ingredients are dissolved with mixing under a nitrogen atmosphere, and the pH checked.

The cooled concentrate is added with gentle mixing under a nitrogen atmosphere to the above-prepared aqueous solution and a sufficient amount of the water for injection is added to a final volume of 10 liters.

The solution is then aseptically filtered under a nitrogen atmosphere, and 1.25 ml is filled into each sterile ampul. Filtered nitrogen gas is introduced into the headspace of each ampul prior to sealing.

We claim:

1. A pharmaceutical dosage form of 1α,25-dihydroxycholecalciferol comprising a therapeutically effective amount of 1α,25-dihydroxycholecalciferol to prevent hypocalcemia solubilized in water with a nonionic surfactant and stabilized with a combination of a metal ascorbate and a chelating agent in the presence of an inert atmosphere at pH 6.4 to 7.8.

2. The pharmaceutical dosage form of claim 1 wherein an excess of said metal ascorbate is present to stabilize said 1α,25-dihydroxycholecalciferol.

3. The pharmaceutical dosage form of claim 1 wherein said 1α,25-dihydroxycholecalciferol is solubilized in water with from 400 to 80,000 parts by weight of a nonionic surfactant, and stabilized with a combination of from 100 to 10,000 parts by weight of a metal ascorbate and from 100 to 10,000 parts by weight of a chelating agent at pH 7.0 to 7.8 in the presence of an inert atmosphere.

4. The pharmaceutical dosage form of claim 3 wherein said metal ascorbate is an alkali or alkaline earth metal ascorbate.

5. The pharmaceutical dosage form of claims 1, 2, 3 or 4 wherein said pH is 7.0 to 7.5.

6. The pharmaceutical dosage form of claims 1, 2, 3 or 4 wherein said pH is 7.0 to 7.3.

7. The pharmaceutical dosage form of claim 1 wherein 1α,25-dihydroxycholecalciferol solubilized in water with 4,000 parts by weight of a nonionic surfactant, and stabilized by a combination of 10,000 parts by weight of a metal ascorbate, 1,000 parts by weight of a chelating agent and an inert atmosphere at pH 7.0 to 7.8.

8. The product of claim 7 wherein said metal ascorbate is an alkaline earth or alkali metal ascorbate.

9. The product of claim 7 wherein said metal ascorbate is sodium ascorbate.

10. The product of claims 7, 8 or 9 wherein said chelating agent is sodium edetate.

11. The product of claims 7, 8, 9 or 10 wherein said inert atmosphere is nitrogen.

12. A pharmaceutical composition which is a dilute, stable, aqueous solution of 1α,25-dihydroxycholecalciferol comprising 1 part by weight of said 1α,25-dihydroxycholecalciferol, 10,000 parts by weight of sodium ascorbate, 4,000 parts by weight of a polysorbate 20 nonionic surfactant, 1,000 parts by weight of disodium edetate, 1,500 parts by weight of sodium chloride, 7,600 parts by weight of sodium phosphate dibasic, 1,840 parts by weight of sodium phosphate monobasic, water q.s. and nitrogen q.s. and having a pH of between 6.4 and 7.8.

13. The solution of claim 12 wherein said pH is between 7.0 to 7.8.

14. The solution of claim 12 wherein said pH is between 7.0 and 7.5.

15. The solution of claim 12 wherein said solution is isotonic.

16. A process for preparing a stable, dilute, aqueous solution of 1α,25-dihydroxycholecalciferol comprising the steps of: preparing a concentrate of said 1α,25-dihydroxycholecalciferol and a nonionic surfactant under an inert atmosphere; preparing an aqueous solution of a metal ascorbate, a chelating agent and a buffering agent under an inert atmosphere, said solution having a pH of from 7.0 to 7.8; and, adding said concentrate to said aqueous, buffered solution, with stirring under an inert atmosphere.

17. The process of claim 16 wherein said aqueous solution additionally comprises sodium chloride.

18. The process of claim 16 or 17 wherein said metal ascorbate is an alkali metal or alkaline earth metal ascorbate and said ascorbate is present in an amount of from 1,000 to 15,000 parts by weight per part of said 1α,25-dihydroxycholecalciferol.

19. The process of claim 16, 17 or 18 wherein said nonionic surfactant is heated to a temperature of from about 50° to 75° C. prior to the addition of said 1α,25-dihydroxycholecalciferol, and said solution is allowed to cool prior to the addition thereof to said aqueous solution.

20. The process of claim 16, 17, 18 or 19 wherein the water used to prepare said aqueous solution is heated to a temperature of between 85° to 100° C. and cooled to a temperature of from about 20° C. to 50° C. prior to the addition of said metal ascorbate, said chelating agent and said buffering agents.

* * * * *